US012597484B2

(12) United States Patent　　　(10) Patent No.: US 12,597,484 B2

Trunck et al.　　　(45) Date of Patent: *Apr. 7, 2026

(54) TRAIT PREDICTION COORDINATION FOR GENOMIC APPLICATION ENVIRONMENT

(71) Applicant: Helix OpCo, LLC, San Mateo, CA (US)

(72) Inventors: Ryan Trunck, Denver, CO (US); Rani Powers, Denver, CO (US); Christopher M. Glode, Denver, CO (US); Stewart Blanford, Littleton, CO (US); Daniel Shin, Denver, CO (US)

(73) Assignee: Helix, Inc., San Mateo, CA (US)

( * ) Notice: Subject to any disclaimer, the term of this patent is extended or adjusted under 35 U.S.C. 154(b) by 1055 days.

This patent is subject to a terminal disclaimer.

(21) Appl. No.: 16/988,965

(22) Filed: Aug. 10, 2020

(65) Prior Publication Data

US 2020/0372970 A1　　Nov. 26, 2020

Related U.S. Application Data

(63) Continuation of application No. 16/289,402, filed on Feb. 28, 2019, now Pat. No. 10,777,300.

(60) Provisional application No. 62/738,763, filed on Sep. 28, 2018.

(51) Int. Cl.

| | |
|---|---|
| *G16B 20/00* | (2019.01) |
| *C12Q 1/68* | (2018.01) |
| *G16B 5/00* | (2019.01) |
| *G16B 40/00* | (2019.01) |
| *G16B 45/00* | (2019.01) |

(52) U.S. Cl.
CPC .............. *G16B 20/00* (2019.02); *C12Q 1/68* (2013.01); *G16B 5/00* (2019.02); *G16B 40/00* (2019.02); *G16B 45/00* (2019.02)

(58) Field of Classification Search
CPC .......... G16B 20/00; G16B 5/00; G16B 40/00; G16B 45/00; G16B 40/20; G16B 50/30; C12Q 1/68
See application file for complete search history.

(56) References Cited

U.S. PATENT DOCUMENTS 5,680,549 A * 10/1997 Raynak ..................... H04L 9/40
709/227

OTHER PUBLICATIONS

Naveed, Muhammad, et al. "Privacy in the genomic era." ACM Computing Surveys (CSUR) 48.1 (2015): 1-44. (Year: 2015).*
Stein, Lincoln D. "The case for cloud computing in genome informatics." Genome biology 11 (2010): 1-7. (Year: 2010).*
Thorvaldsdóttir, Helga, et al. "A genomic data viewer for iPad." Genome biology 16 (2015): 1-6. (Year: 2015).*
Lucivero, Federica, and Barbara Prainsack. "The lifestylisation of healthcare?'Consumer genomics' and mobile health as technologies for healthy lifestyle." Applied & translational genomics 4 (2015): 44-49. (Year: 2015).*

* cited by examiner

*Primary Examiner* — Larry D Riggs, II
*Assistant Examiner* — Kettip Kriangchaivech
(74) *Attorney, Agent, or Firm* — Duft & Bornsen, PC

(57)　　　ABSTRACT

Systems and methods are provided for trait prediction coordination. One embodiment is a method that includes launching a genomics application at a user device, receiving a command to present a partner application within the genomics application, selecting characteristics to predict for an individual, based on an identifier that distinguishes the partner application from other partner applications, operating polygenic models that generate predictions for the characteristics based on genetic records for the individual, acquiring media for the partner application, based on the predictions, and operating the partner application to update a display at the user device with the media, thereby providing the predictions in a format specific to the partner application.

26 Claims, 11 Drawing Sheets

GENERATING PREDICTIONS FOR PARTNER APPLICATIONS – REPLACING OUT DATED PREDICTIONS

CHARACTERISTICS TO PREDICT

| APP ID | PREDICTIONS REQUESTED |
|---|---|
| HI_FIT | CARDIAC HEALTH, MUSCLE TONE, WEIGHT |
| FAMILY_HISTORY | ANCESTRY |
| HEALTH_MASTER | CARDIAC HEALTH, CANCER RISK, IMMUNE RESPONSE |
| TASTE_ASSISTANT | BITTERNESS SENSITIVITY, CILANTRO TASTE |

GENETIC RECORDS STORED FOR INDIVIDUALS

| TARGET ID | GENETIC RECORD TYPE | GENETIC RECORD ID(S) |
|---|---|---|
| AMYWINTERS505 | MICROARRAY | 156165163 |
| SIMONCHAN85 | WHOLE GENOME | 654166515 |
| CARLA412 | WHOLE GENOME | 651651651 |
| GREGORYMASTERS | SNP(25843), SNP(58681) | 878913198, 154739513 |

MODELS FOR PREDICTIONS

| CHARACTERISTIC | MODEL | TARGET GROUP |
|---|---|---|
| LACTOSE INTOLERANCE | 415_WHOLE_GENOME_1 | INDIVIDUALS WITH WHOLE GENOME RECORDS |
| EYE COLOR | 163_MICROARRAY_1 | INDIVIDUALS WITH MICROARRAY RECORDS |
| EYE COLOR | 514_WHOLE_GENOME_POP1 | INDIVIDUALS WITH WHOLE GENOME RECORDS IN POPULATION 1 |
| EYE COLOR | 991_WHOLE_GENOME_POP2 | INDIVIDUALS WITH WHOLE GENOME RECORDS IN POPULATION 2 |
| DIVING PROFICIENCY | 1506_WHOLE_EXOME | INDIVIDUALS WITH EXOME RECORDS |

STORED PREDICTIONS

| TARGET ID | CHARACTERISTIC | PREDICTION | MODEL | VERSION |
|---|---|---|---|---|
| AMYWINTERS505 | EYE COLOR | ALLELE DATA, VALUE, INTERVAL, KEY | 514_WHOLE_GENOME_POP1 | 1.20 |
| AMYWINTERS505 | LACTOSE INTOLERANCE | ALLELE DATA, VALUE, INTERVAL, KEY | 415_WHOLE_GENOME_1 | 1.19 |
| AMYWINTERS505 | SKIN SENSITIVITY | ALLELE DATA, VALUE, INTERVAL, KEY | 962_WHOLE_GENOME | 1.22 |
| JONATHANDOE12 | CARDIAC HEALTH | ALLELE DATA, VALUE, INTERVAL, KEY | 221_MICROARRAY | 1.22 |
| MARCUSRONSON41 | BLUSH RESPONSE | ALLELE DATA, VALUE, INTERVAL, KEY | 71_EXOME | 1.05 |

GENOMICS APPLICATION CONTENT AT USER DEVICE

```
GENOMICS APPLICATION
        EXECUTABLE FILE
        RESOURCES
                LIBRARY 1
                LIBRARY 2
                CONFIGURATION FILE 1
                PARTNER APP 1 ICON
                URI CALL TO PARTNER APP 1
                PARTNER APP 2 ICON
                URI CALL TO PARTNER APP 2
                PARTNER APP 3 ICON
                URI CALL TO PARTNER APP 3
```

FIG. 12

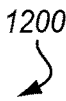

1200

PARTNER APPLICATION CONTENT AT CONTENT MANAGEMENT SERVER

```
CONTENT MANAGEMENT SERVER
        PARTNER APP 1
                URI
                JSON (SPLASH SCREEN)
                        IMAGES
                        VIDEO
                        TEXT
                        UI ELEMENTS
                JSON (ANALYSIS SCREEN)
                        IMAGES
                        VIDEO
                        AUDIO
                        FRAMING TEXT
                        PREDICTION TEXT
                        UI ELEMENTS
                JSON (FEEDBACK SCREEN)
                        IMAGES
                        VIDEO
                        TEXT
                        UI ELEMENTS
```

TRAIT PREDICTION COORDINATION FOR GENOMIC APPLICATION ENVIRONMENT

FIELD

The disclosure relates to the field of genomics, and in particular, to predicting traits of individuals based on their genetics.

BACKGROUND

The genome of an individual defines phenotypic traits (i.e., observable traits) for a staggering array of characteristics ranging from eye color to muscle tone to dietary sensitivity. Specifically, the expression of genes in various forms of Deoxyribonucleic Acid (DNA), Ribonucleic Acid (RNA), and protein may result in a specific phenotype being expressed by an individual. Even portions of the genome which are not directly linked to known phenotypic traits may provide valuable insights. For example, these portions of the genome may be used to determine the ancestry of an individual. Genetic factors therefore play a major role in defining how the human body functions, and also in defining variations between individuals.

While biological inheritance of physical traits has been studied for decades, associating specific phenotypes with specific nucleotide sequences or combinations thereof remains a complicated process. The human genome itself occupies approximately eighty Gigabytes (GB) of data. Furthermore, there are estimated to be roughly ten million Single Nucleotide Polymorphisms (SNPs) within the genome. Large stretches of the genome include non-coding regions (e.g., introns) as well as coding regions (e.g., exons), and the non-coding regions may regulate how one or more coding regions are expressed. Thus, in addition to coding regions, even variations in non-coding regions may have an impact on phenotype, and false positives may occur when attempting to determine the combination of nucleotide sequences that result in a specific phenotype. For example, genes that result in expression of a first trait (e.g., hair color) may be expressed more readily in one population than another. That population may also have genes that result in expression of additional traits. The genes that regulate expression of the additional traits are therefore highly correlated with the genes that regulate expression of the first trait. This means that there is a chance of mistakenly assuming that the genes which regulate expression of the additional traits are used to regulate expression of the first trait. For at least these reasons, the process of correlating specific variations in the genome with specific phenotypes for a characteristic can be fiendishly complex.

Further increasing the complexity of this process, it is not possible to identify many traits of an individual without studying the individual closely, and some traits may be hard to precisely quantify (e.g., hair curl, personality, etc.). Other traits may be hard to identify based on information currently known about the individual. For example, an individual who has constant headaches may be suffering from high blood pressure, high stress, allergies, or other conditions. Without more information, it would be impossible to determine which nucleotide sequences within that individual are correlated with (and/or contribute to) the reported traits.

Models have been built which attempt to predict the traits of an individual based on genetic records for that individual. However, the creation of such models is a time-consuming and labor-intensive process. This disincentivizes many entities from providing trait prediction services that are in-depth and scientifically robust. Thus, a bewildering array of entities are currently providing trait prediction services that have varying or unknown levels of quality. Hence, individuals may find themselves intimidated by the untamed ecosystem for trait prediction. Even those individuals who move forward with trait prediction need to subscribe to multiple services in order to receive predictions for all desired traits. This necessitates the transmission and sharing of genetic records across a wide number of entities, which increases the risk of genetic records being stolen or accessed without authorization.

Hence, those who desire personalized trait predictions continue to seek out enhanced systems and methods for achieving these goals.

SUMMARY

Embodiments described herein maintain genetic records and polygenic models for trait prediction in a centralized repository. Users may download a genomics application that interacts with the repository. Within the genomics application, one or more partner applications are provided. Each partner application may be provided by a different entity, may include its own unique content, and may utilize predictions from the repository for a unique set of characteristics. This means that genomic insights may be provided by many different entities, while genetic records remain safely stored in the repository. Furthermore, a user may purchase any desired combination of partner applications in order to receive desired trait predictions in desired formats, and may access these partner applications via a single entry point (i.e., the genomics application) without needing to log into separate accounts. Because partner applications are presented within the genomics application, users intuitively understand that the partner applications are held to certain quality and privacy standards (e.g., standards enforced by the provider of the genomics application). In one embodiment, the provider of the genomics application ensures that partner applications meet a threshold level of quality, and implements security protocols to ensure that predictions are securely provisioned to partner applications on a need-to-know basis.

One embodiment is a system that includes a user device. The user device includes a memory that stores a genomics application. The user device also includes a controller that launches the genomics application, receives a command to present a partner application within the genomics application, and generates a request that refers to an individual and includes an identifier which distinguishes the partner application from other partner applications. The user device further includes an interface that transmits the request. The system further includes an application coordination server. The server includes an interface that receives the request, and a controller that selects characteristics to predict for the individual based on the identifier, that coordinates operation of polygenic models that generate predictions for the characteristics based on genetic records for the individual, and that generates a response to the request that includes the predictions. The controller of the user device additionally acquires media for the partner application based on the predictions, and operates the partner application to update a display at the user device with the media, thereby providing the predictions in a format specific to the partner application.

A further embodiment is a method that includes launching a genomics application at a user device, receiving a command to present a partner application within the genomics application, selecting characteristics to predict for an individual, based on an identifier that distinguishes the partner application from other partner applications, operating polygenic models that generate predictions for the characteristics based on genetic records for the individual, acquiring media for the partner application, based on the predictions, and operating the partner application to update a display at the user device with the media, thereby providing the predictions in a format specific to the partner application.

A still further embodiment is a non-transitory computer readable medium embodying programmed instructions which, when executed by a processor, are operable for performing a method. The method includes launching a genomics application at a user device, receiving a command to present a partner application within the genomics application, selecting characteristics to predict for an individual, based on an identifier that distinguishes the partner application from other partner applications, operating polygenic models that generate predictions for the characteristics based on genetic records for the individual, acquiring media for the partner application, based on the predictions, and operating the partner application to update a display at the user device with the media, thereby providing the predictions in a format specific to the partner application.

Other illustrative embodiments (e.g., methods and computer-readable media relating to the foregoing embodiments) may be described below. The features, functions, and advantages that have been discussed can be achieved independently in various embodiments or may be combined in yet other embodiments further details of which can be seen with reference to the following description and drawings.

DESCRIPTION OF THE DRAWINGS

Some embodiments of the present disclosure are now described, by way of example only, and with reference to the accompanying drawings. The same reference number represents the same element or the same type of element on all drawings.

FIG. 7 is a table illustrating characteristics to predict on an application-by-application basis, in an illustrative embodiment.

FIG. 8 is a table listing genetic records stored for individuals in an illustrative embodiment.

FIG. 9 is a table listing polygenic models for making predictions in an illustrative embodiment.

FIG. 10 is a table illustrating predictions stored for individuals in an illustrative embodiment.

FIG. 11 illustrates content stored for a genomics application at a user device in an illustrative embodiment.

FIG. 12 illustrates content stored for a partner application at a content management server in an illustrative embodiment.

DESCRIPTION

The figures and the following description depict specific illustrative embodiments of the disclosure. It will thus be appreciated that those skilled in the art will be able to devise various arrangements that, although not explicitly described or shown herein, embody the principles of the disclosure and are included within the scope of the disclosure. Furthermore, any examples described herein are intended to aid in understanding the principles of the disclosure, and are to be construed as being without limitation to such specifically recited examples and conditions. As a result, the disclosure is not limited to the specific embodiments or examples described below, but by the claims and their equivalents.

Figure 1:
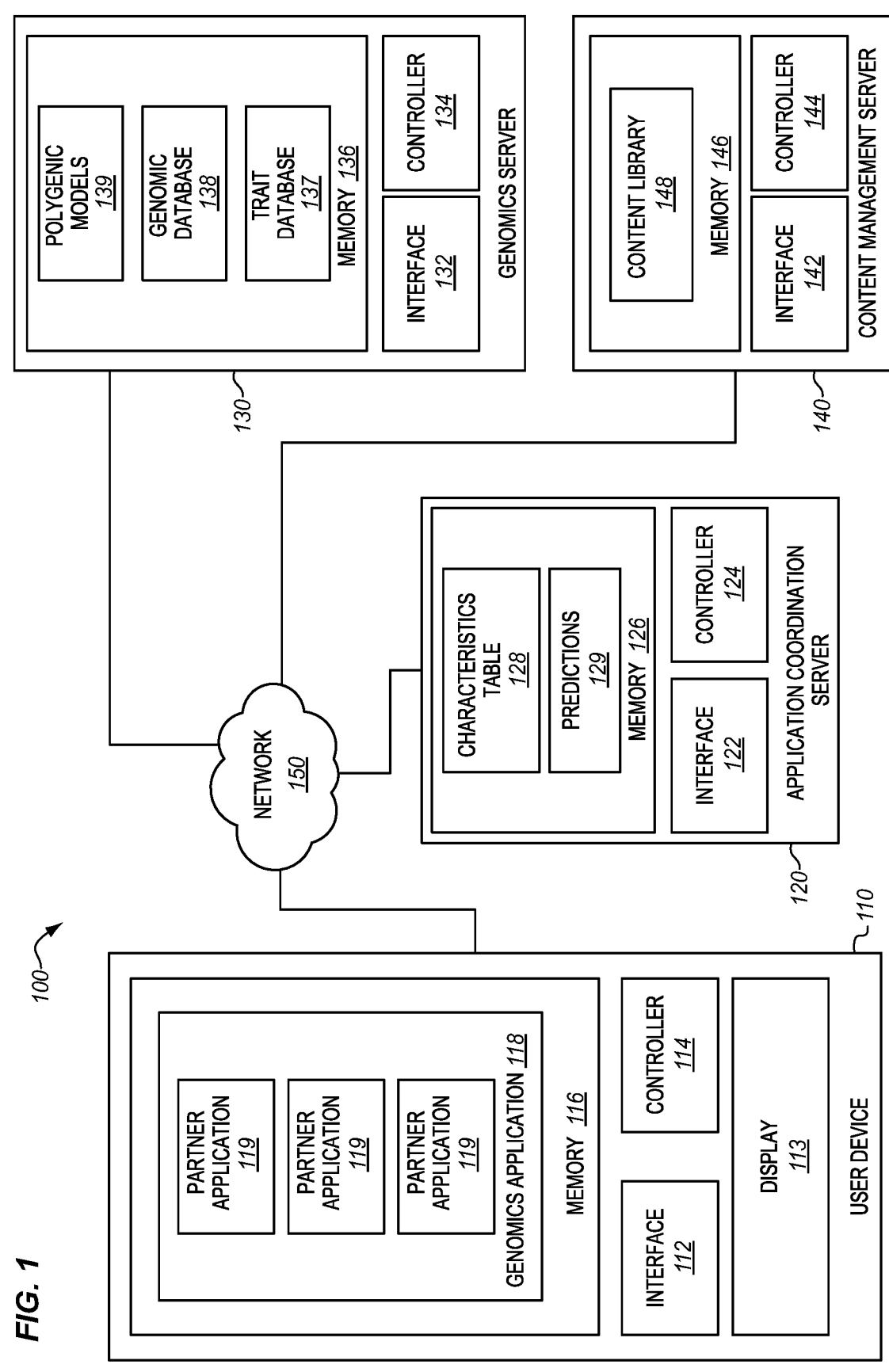
FIG. 1 is a block diagram of a trait prediction system wherein a genomics application at a user device provides access to multiple partner applications in an illustrative embodiment.

FIG. 1 is a block diagram of a trait prediction system 100 in an illustrative embodiment. Trait prediction system 100 comprises any system that operates polygenic models to make predictions about individuals based on genetic records for those individuals. Trait prediction system 100 has been enhanced with regard to prior systems in order to provide a genomics application from which many partner applications can be launched. Each partner application may be sourced by a different entity, and may provide uniquely tailored insights that are based on the genetic records of an individual. Partner applications may even be sourced by the provider of the genomics application itself.

In this embodiment, trait prediction system 100 includes user device 110 (e.g., a desktop, laptop, cellular phone, tablet, etc.), application coordination server 120, genomics server 130, and content management server 140, which are coupled for communication via network 150 (e.g., the Internet, a combination of small networks, etc.).

User device 110 generates requests for predictions that are based on genetic records, and presents those predictions via display 113 (e.g., a haptic display). User device 110 includes interface 112, controller 114, and memory 116. Controller 114 manages the operations of user device 110 in accordance with instructions stored in memory 116. For example, controller 114 may generate login information, commands, authorizations, and/or request user feedback for processing by application coordination server 120. Memory 116 stores genomics application 118, which includes instructions for communicating with application coordination server 120 in order to predict the characteristics of individuals.

As used herein, a "characteristic" of an individual is a category in which an individual may vary from other individuals, and includes phenotypic characteristics. Examples of characteristics include hair color, eye color, height, resting heart rate, dietary sensitivity to gluten, etc. Characteristics may also include demographics such as ancestry, age, or sex.

Genomics application 118 also manages the acquisition and distribution of predictions for partner applications 119, which are presented within genomics application 118. While only one user device 110 is depicted in FIG. 1, any suitable number of user devices (e.g., millions of user devices) may be placed into communication with the rest of the components of trait prediction system 100. Each user device 110 may store a copy of genomics application 118, as well as one or more partner applications 119. The number and type of partner applications 119 may vary between copies of genomics application 118. For example, one copy of genomics application 118 accessed by a first user may store a first set of partner applications owned by that user, another copy accessed by a second user may store a second set of partner applications owned by the second user, etc.

Application coordination server 120 receives requests for predictions from user devices 110, and directs genomics server 130 to generate predictions based on the received requests. Application coordination server 120 includes interface 122, controller 124, and memory 126. Controller 124 manages the operations of application coordination server 120 in accordance with instructions stored in memory 126. For example, controller 124 may analyze login information provided by a user device 110 to identify individuals (and/or characteristics) for which predictions are permitted to be made, and may select or otherwise coordinate polygenic models that will be used by genomics server 130 to generate predictions.

Memory 126 also stores characteristics table 128, as well as predictions 129. Characteristics table 128 indicates which characteristics are desired for prediction, on an application-by-application basis. For example, characteristics table 128 may indicate that one partner application for cosmetics seeks predictions for characteristics such as eye color, skin sensitivity, and eyelash length, while another partner application for fitness seeks predictions for characteristics relating to resting heart rate, muscle tone, and Body Mass Index (BMI). This information may be used to select polygenic models that will generate predictions, as discussed above. Predictions 129 comprise predictions that have already been made for one or more individuals at a previous point in time. Predictions 129 in memory 126 are populated as new predictions are generated by the polygenic models. Hence, the number of predictions 129 for a given individual will at first be zero, and then will increase in number as more predictions are made for the individual by genomics server 130.

Genomics server 130 generates predictions for the characteristics of individuals based on genetic records for those individuals. Genomics server 130 includes interface 132, controller 134, and memory 136. Controller 134 manages the operations of genomics server 130 in accordance with instructions stored in memory 136. Memory 136 further stores genomic database 138 and polygenic models 139. Hence, memory 136 acts as a centralized repository of genomic information.

Genomic database 138 includes records that describe genetic variants found in one or more specific individuals. As used herein, the term "genetic variant" refers to a variation of an individual gene (e.g., a variation in alleles, a Single Nucleotide Polymorphism (SNP), a Single Nucleotide Variant (SNV), etc.), and also includes epigenetic variations, variations in nucleotides that regulate gene expression or gene activity, etc. A "variation" as used herein need not refer to a deviation from a predefined standard or expected value, but rather refers to a piece of genomic information that is distinct from other pieces of genomic information that could occupy the same loci in the genome (loci in the genome are hereinafter referred to as "genetic loci").

Each record in genomic database 138 indicates genetic variants (or other genomic information) for one or more specific individuals. For example, a first record may provide a first portion of an individual's genome, a second record may provide a second portion of the individual's genome, etc. In further embodiments, records provide genomic information on an individual-by-individual basis. For example, a first record in genomic database 138 may indicate genetic variants found within a first individual, a second record in genomic database 138 may indicate genetic variants found within a second individual, etc. In a further example, a single record in genomic database 138 may report the existence (or non-existence) of a specific genetic variant across an entire population (e.g., millions) of specified individuals. When organized as a table, such a record may include one row for each individual in the population. A first row provides genomic information for a first individual (e.g., to indicate the existence or nonexistence of a genetic variant), a second row provides the same type of genomic information for a second individual, and so on for an entire population. Records that store genomic information may also be referred to herein as "genetic records."

Controller 134 uses information from genomic database 138 as input to one or more polygenic models 139 that generate predictions for characteristics of an individual. A polygenic model makes predictions (e.g., predicting the value of a characteristic, predicting the existence or nonexistence of a phenotypic trait, etc.) for individuals based on their genomic information. Each polygenic model expects input indicating the existence (or nonexistence) of specific genetic variants for an individual in order to generate a prediction. For example, each polygenic model may expect to receive information describing genetic variants for an individual that occupy predetermined genetic loci. The predetermined genetic loci may be indicated as locations on a chromosome, locations within the genome as a whole, a range of locations on a chromosome, etc. The predetermined genetic loci for which input is expected may vary between polygenic models. For example, one polygenic model may expect information describing three Single Nucleotide Polymorphisms (SNPs) at three separate predetermined genetic loci on a certain single chromosome, another polygenic model may expect sequences of nucleotides that each occupy a range of predetermined genetic loci on a different chromosome of an individual, and yet another polygenic model may expect information describing genetic variants for millions of genetic loci across the genome of an individual. The number and position of predetermined genetic loci considered by each model may therefore vary widely.

Polygenic models 139 may comprise machine learning models (e.g., neural networks, etc.) that have already been trained based on a vetted set of training data, may comprise other predictive models (e.g., genetic algorithms, statistical models, linear or non-linear models, other stochastic or deterministic models, etc.). Any suitable number of polygenic models 139 may be utilized by genomics server 130. Different models may generate predictions for different characteristics. Additionally, different models may generate predictions for the same characteristic.

Each polygenic model 139 that generates predictions for the same characteristic may perform a different analysis of genetic variants when generating a prediction. For example, different polygenic models for the same characteristic may weigh certain genetic variants differently when making a prediction, or may perform different calculations based upon the genetic variants of an individual. The polygenic models 139 may also be differentiated based on the type and amount of genomic information expected as input (e.g., whole genome vs. exome vs. microarray). Polygenic models 139 may even be differentiated based on the data that was used to train them. Different sets of training data may describe characteristics and genes of different individuals in the same demographic, or individuals in different demographics. When polygenic models have been calibrated for different demographics, the overall accuracy of predictions made for an individual may be beneficially increased by selecting a polygenic model calibrated for the demographics of that individual.

Trait database 137 stores records which indicate the traits of individuals for specific characteristics. For example, a record in trait database 137 may indicate that for the characteristic of hair color, an individual has the trait of "brown haired." In further embodiments, records may include Electronic Health Records (EHRs) of an individual, a pulse rate of an individual over time during a workout, a level of cardiovascular health, or even a pattern of purchases by an individual that suggest a specific trait, such as near-sightedness, acid reflux, diving proficiency, etc. In still further embodiments, trait database 137 may even include records describing behaviors of individuals. The behaviors may include fitness activities, dietary habits, travel patterns, social networking activities and preferences (e.g. "Likes" of a sports team or political party), purchases, medical treatments, etc. Records in trait database 137 may be organized for individuals or for entire populations in a similar manner as described above for records in genomic database 138. These records may also be updated based on user feedback, and/or used for training polygenic models 139.

While polygenic models 139 expect genomic information for multiple loci as input in order to generate predictions, in further embodiments controller 134 may also use the traits of an individual (found in trait database 137) as additional inputs to the polygenic models in order to increase the accuracy of generated predictions.

Controller 134 utilizes records in genomic database 138, optionally in combination with records in trait database 137, as inputs to one or more polygenic models 139, and generates predictions regarding individuals based on the output of these models. Each polygenic model 139 may attempt to predictively assign a trait to an individual for a given characteristic, based on the genotype and/or characteristics of that individual. Controller 134 may direct interface 132 to provide these predictions to application coordination server 120 for distribution.

Content management server 140 delivers media (e.g., text, images, audio, video, etc.) for distribution to user devices 110. When a content request for a partner application is received at interface 142, controller 144 accesses content library 148 stored in memory 146 to identify corresponding media. The media is then transmitted to the device that sourced the content request via interface 142. The type and amount of media provided may vary depending on the partner application that is associated with the content request.

The controllers described herein may each be implemented, for example, as custom circuitry, as a hardware processor executing programmed instructions, or some combination thereof. The interfaces described herein are capable of receiving and transmitting data via network 150, and may each comprise any suitable components for conveying data, such as an Ethernet port, a wireless transceiver compatible with Institute of Electrical and Electronics Engineers (IEEE 802.11 protocols), Bluetooth standards, etc. The memories described herein may each comprise any suitable devices capable of storing and retrieving data for an electronic device, such as magnetic Hard Disk Drives (HDDs), Solid State Drives (SSDs), Random Access Memory (RAM), etc. The servers described herein may be implemented as stand-alone servers, may be implemented as part of a distributed cloud computing system such as Amazon Web Services (AWS), may comprise physical hardware implementing one or virtual machines to perform desired operations, etc. Furthermore, the various servers and user devices described herein may be located remotely from each other (e.g., hundreds of miles from each other).

Illustrative details of the operation of trait prediction system 100 will be discussed with regard to FIG. 2. Assume, for this embodiment, that a user has accessed trait prediction system 100 in order to make personalized predictions for an individual, based on the genetic variants of that individual. In many embodiments, the individual and the user are one and the same. However, in some embodiments the user is distinct from the individual. For example, the user may be a family member of, or medical practitioner for, the individual.

Figure 2:
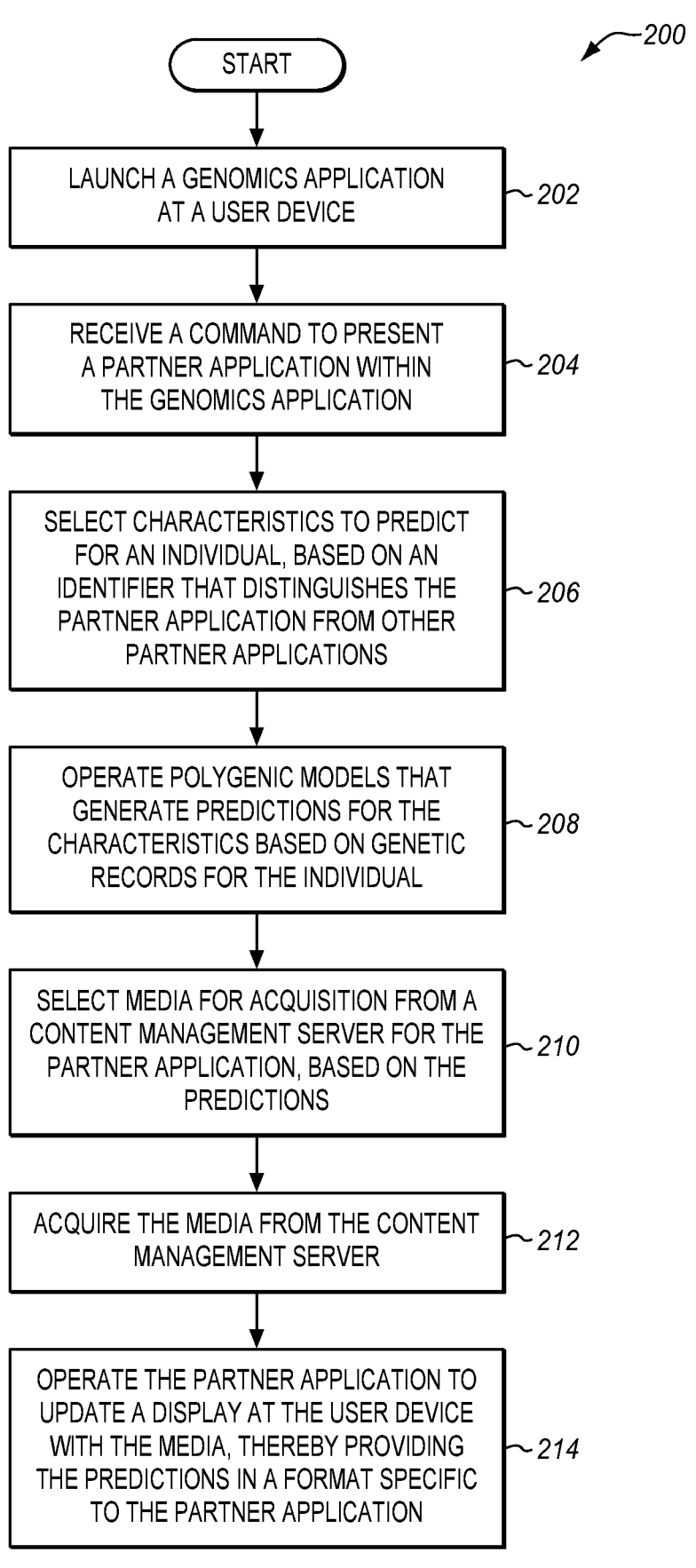
FIG. 2 is a flowchart illustrating a method for operating a trait prediction system in an illustrative embodiment.

FIG. 2 is a flowchart illustrating a method 200 for operating a trait prediction system in an illustrative embodiment. The steps of method 200 are described with reference to trait prediction system 100 of FIG. 1, but those skilled in the art will appreciate that method 200 may be performed in other systems. The steps of the flowcharts described herein are not all inclusive and may include other steps not shown. The steps described herein may also be performed in an alternative order.

In step 202, the user launches genomics application 118 on user device 110. Launching genomics application 118 may comprise selecting an icon which causes controller 114 to execute instructions stored in memory for genomics application 118. After loading, genomics application 118 may update display 113 with a main menu depicting genomic insights, news related to genomics, and icons for one or more partner applications 119. Depending on the type of genomic insights desired by the user, the user selects an icon for a partner application. The user has access to multiple different partner applications 119 via genomics application 118, and selects a partner application 119 focused on an aspect of the individual's genome which they are presently curious about. The user may further activate an icon displayed on genomics application 118 that is associated with the selected partner application. In this manner, user interactions with genomics application 118 may cause controller 114 to generate commands for loading the selected partner application.

In step 204, controller 114 receives a command to present the selected partner application within genomics application 118. As used herein, a partner application is presented within genomics application 118 when loading of the partner application is triggered by user interaction with genomics application 118, when the partner application is graphically interrelated with the genomics application 118 as shown on display 113 (e.g., as a sub-window within a window for the genomics application 118, as a window that springs from a window from the genomics application 118, as a window that returns to the genomics application 118 when closed, etc.), and/or when instructions performed for the partner application are serviced via the genomics application 118. In one embodiment, instructions for the selected partner application are processed via the genomics application 118.

In response to receiving the command, controller 114 initiates a process for loading the selected partner application for display. The process includes retrieving predictions for the individual via application coordination server 120, and retrieving media for the partner application based on the predictions, via content management server 140. To initiate the process, controller 114 may generate a request for predictions. The request includes an identifier that distinguishes the selected partner application from other partner applications (e.g., partner applications prepared by other entities) ("app ID"), an identifier for the individual ("target ID"), and an authorization token identifying the user. This request may be encrypted and provided to application coordination server 120. Interface 122 of application coordination server 120 receives the request, and controller 124 confirms that the user is authorized to make predictions for the individual.

In step 206, controller 124 selects characteristics to predict for the individual, based on the app ID. In one embodiment, controller 124 consults characteristics table 128 in order to determine which characteristics to predict. Controller 124 may further consult genomics server 130, or information stored in memory 126, in order to determine one or more tags associated with the individual that predictions are being made for. The tags may indicate demographics of the individual, preferences of the individual or user, an amount or type of genomic information that is presently stored for the individual, etc. If multiple polygenic models exist for predicting a characteristic of the individual, the tags may be used by controller 124 to select an appropriate model. In one embodiment, controller 124 directs interface 122 to transmit a list of selected polygenic models, as well as the target ID, to interface 132 of genomics server 130.

In step 208, controller 134 operates polygenic models 139. The polygenic models generate predictions for the characteristic based on genetic records for the individual. In one embodiment, controller 134 selects which polygenic models to use in a similar manner as described for controller 124 above. In further embodiments, controller 134 operates polygenic models at the direction of controller 124. Controller 134 retrieves relevant genetic records (e.g., any suitable genetic records which include genomic information used as an input for the current model), provides genomic information in the records to a polygenic model for predicting the characteristic, and operates the model to generate a prediction. For example, if the polygenic model is implemented as a neural network, controller 134 may apply individual pieces of genomic information describing genetic variants of the individual to input nodes in an input layer of the neural network, and generate a prediction based on the results of one or more output nodes in an output layer of the neural network. A prediction may indicate a trait assigned for a characteristic (e.g., brown eyes, not lactose intolerant, brown hair), may include an expected accuracy of the prediction, and may also include a confidence interval for the prediction.

After the predictions have been made, controller 134 operates interface 132 to provide the predictions to application coordination server 120. Controller 124 provides each prediction (e.g., in its entirety, or an abridged version thereof) to user device 110, and may further store the predictions in memory 126 for future reference. Any communications that include the predictions may be encrypted to ensure privacy.

After receipt of the predictions for the individual, controller 114 may generate a request directed to content management server 140. The request may include the app ID, and may indicate each prediction that content should be retrieved for. The request may omit the target ID. This ensures that even if the communication is intercepted, a malicious entity will be unable to determine who the predictions relate to.

Controller 144 receives the request via interface 142. In step 210 controller 144 selects media for acquisition from content management server 140 for the selected partner application, based on the predictions. This may comprise selecting media within content library 148 that is flagged as relating to both the app ID and one of the predictions. Controller 144 proceeds to retrieve the selected media from content library 148. Interface 142 provides the retrieved media to user device 110.

In step 212, interface 112 acquires the media from the content management server 140. Controller 114 generates instructions for updating the display 113 based on this acquired media. In step 214, controller 114 operates the selected partner application to update display 113 with the media, thereby providing predictions in a format (e.g., visual arrangement, theme) specific to the partner application. Updating the display 113 may comprise providing commands to alter the color or intensity of pixels at the display 113 in order to revise the visual output of display 113.

Method 200 may be performed multiple times via a single user device in order to load multiple partner applications, or to receive new information for new individuals. In this manner, controller 114 may receive and service multiple commands to present partner applications within genomics application 118, each command referring to a different partner application. Furthermore, method 200 may be performed asynchronously by many (e.g., tens of thousands) of user devices 110 in order to acquire predictions for a variety of individuals. Application coordination server 120 may service these requests from the user devices in order to ensure both prompt and secure delivery of predictions on a massive scale.

The techniques provided above provide various technical benefits with respect to genomic and bioinformatic technology. First, it enables partners to provide genomic insights to users without having to create their own polygenic models, which increases the ability of partners who are not genomic experts to engage with users. This aspect also assures users that polygenic models come from a centralized, expert source, while partners remain capable of independently updating information and reports provided to users via the content management server. It also reduces the amount of labor and expertise needed by partners in order to develop applications that provide insights that are both in-depth and robust. This ability to engage in accelerated or bootstrapped development enhances the ability of partners to keep respective partner applications up to date and relevant. Second, because partner applications are presented as part of a single ecosystem within the genomics application, users have a "one-stop shop" for retrieving genomic insights. This increases consumer confidence by associating partners with the reputation of a single well-known entity. Third, users may use a single service to receive insights for a variety of characteristics. This eliminates the need for users to track multiple accounts and passwords, and enhances security by limiting when and where genomic information is shared. In fact, using the systems above, genetic records do not need to be transmitted along a network in order for a user to receive predictions, even though many entities may provide partner applications. This is because the genomic database is safely stored at a genomics server, which generates predictions without having to receive genetic records from other entities, or provide those records to third parties (e.g., partners).

Still further, the techniques provided herein enable rapid scaling to any suitable number of users, and are performed dynamically, in that processing performed on genetic records is not predetermined, but rather dynamically decided based on a user's actions with partner applications. Hence, the techniques and systems described herein are capable of rapidly accounting for changes as trait predictions are refined, are widely adaptable for many types of models, and permits tailoring of polygenic models to specific populations by using corresponding training data sets. Even further, the technologies of bioinformatics and genomics are enhanced via the use of these techniques, because the techniques described herein enable greater granularity and diversity of prediction services to users, on a personalized basis and without requiring that parties each develop their own predictive model. For example, centralized control of predictive models ensures that quick and efficient version control can be applied to those predictive models, which is valuable because predictive models constantly evolve as new data sets for new populations are acquired. In a further example, separating models from the partners that wish to provide trait prediction applications results in a benefit, because the same trait prediction can be reported in different ways. That is, a trait prediction for lactose tolerance may be reported as a set of dietary guidelines via a fitness application (e.g., "you can enjoy milk and dairy products to fulfill your calorie requirements"), while the same trait prediction may be reported for its historical relationship to animal husbandry via an ancestry application (e.g., "lactose tolerance evolved in European populations because it provided a substantial benefit for those who engaged in animal husbandry"). Different partners may therefore focus on different aspects and insights related to trait prediction, without having to generate the predictive models themselves.

Figure 3:
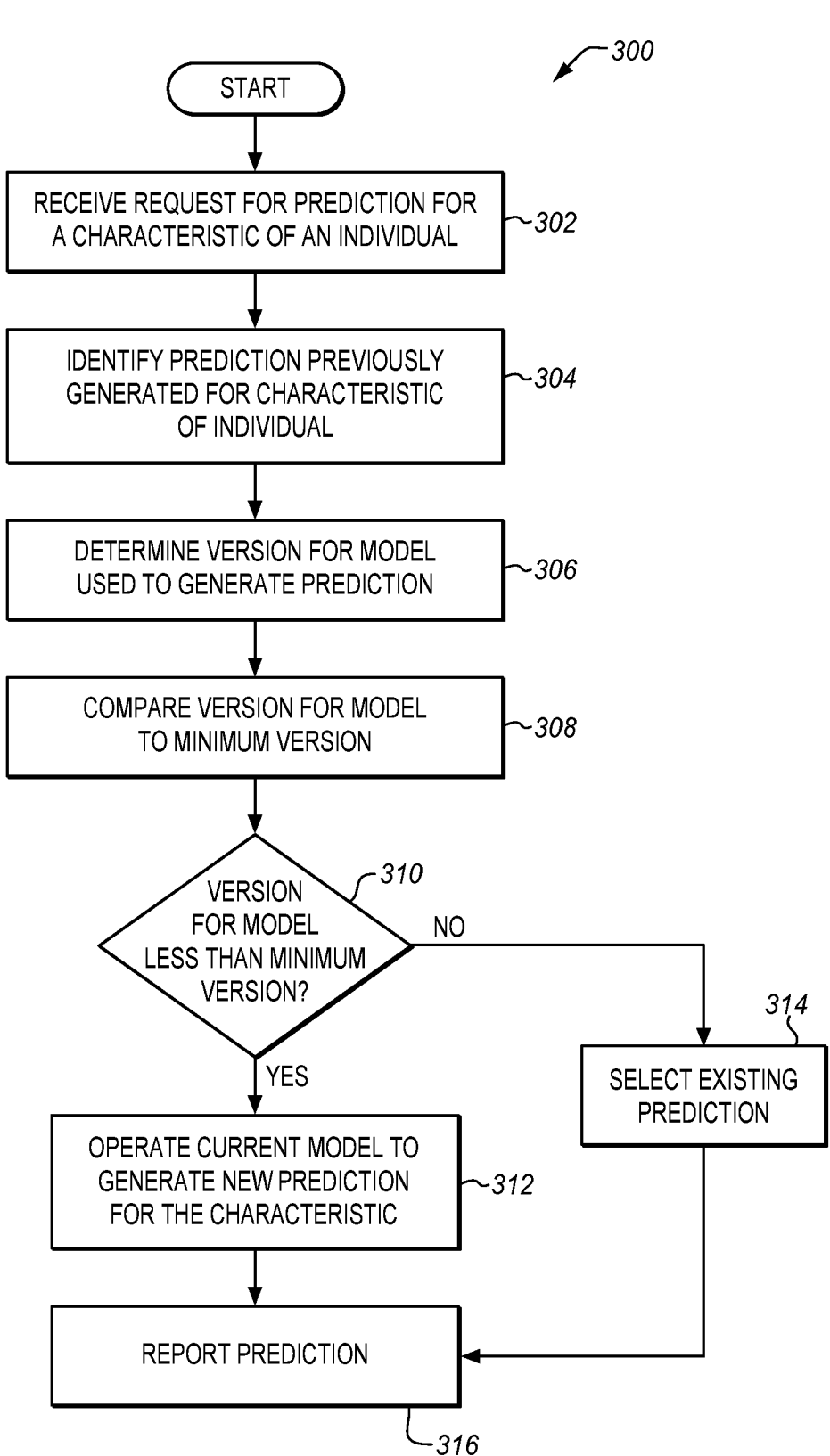
FIG. 3 is a flowchart illustrating a method for selectively foregoing operation of polygenic models in an illustrative embodiment.

FIG. 3 is a flowchart illustrating a method 300 for selectively foregoing operation of polygenic models in an illustrative embodiment. Method 300 may be performed, for example, during step 208 of method 200 described above.

In step 302, controller 124 of application coordination server 120 receives a request to predict a characteristic of an individual. In step 304, controller 124 identifies a prediction that has previously been generated for the characteristic of the individual. This may comprise controller 124 consulting predictions 129. In step 306, controller 124 determines a version for the model that was used to generate the identified prediction. This version may be a version of the model itself, the version of a library in which the model is included, etc. In step 308, controller 124 compares the version for the model that generated the identified prediction to a minimum version. The minimum version may be indicated on an application-by-application basis in memory 126, or may be indicated in the request itself.

If the version for the model is less than the minimum version (step 310), then the prediction is out-of-date. Thus, controller 124 contacts genomics server 130, which operates a current polygenic model for the characteristic to generate a new prediction. Alternatively, if the version for the model is equal to or greater than the minimum version (step 310), then controller 124 selects the already-existing prediction in memory 126 and foregoes operating the polygenic model for the characteristic. The prediction is then reported back to the device that generated the request in step 316.

Figure 4:
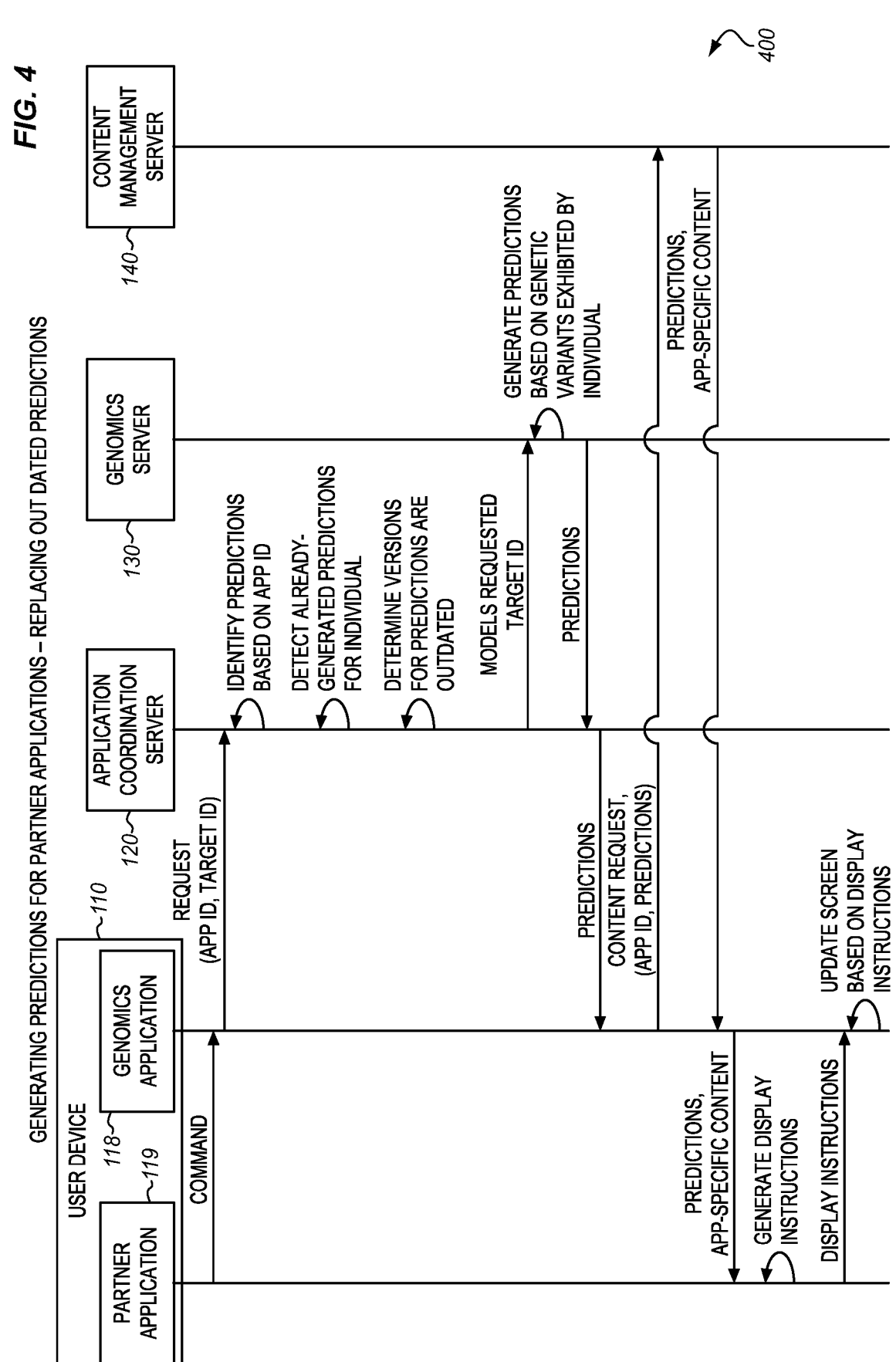
FIG. 4 is a message diagram illustrating interactions between components of a trait prediction system operating in accordance with the method of FIG. 3 in an illustrative embodiment.
Figure 5:
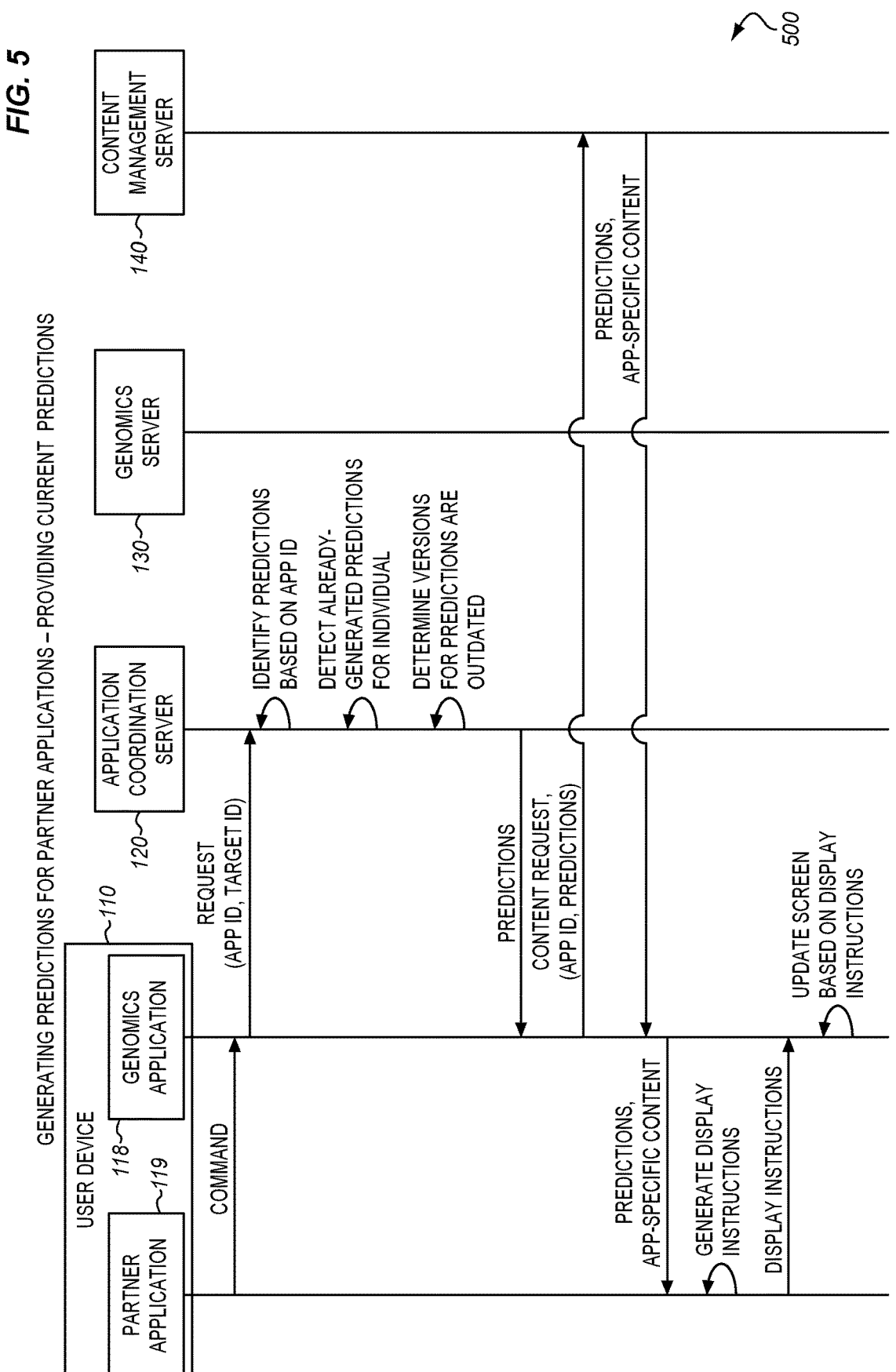
FIG. 5 is a message diagram illustrating interactions between components of a trait prediction system operating in accordance with the method of FIG. 3 in a further illustrative embodiment.

FIGS. 4-5 illustrate communications between the various components described above, for example when selectively foregoing the generation of new predictions for an individual. FIG. 4 is a message diagram illustrating interactions between components of a trait prediction system operating in accordance with the method of FIG. 3 in an illustrative embodiment. According to FIG. 4, user interaction with a partner application (e.g., an icon for a partner application, presented at genomics application 118) results in a command at genomics application 118. Genomics application 118 generates a request including an app ID and target ID, which is passed to application coordination server 120.

The application coordination server 120 determines which characteristics should be predicted based on the app ID, and detects the presence of already-generated predictions for those characteristics. However, because the predictions are outdated, new predictions are acquired from genomics server 130. The predictions are used by genomics application 118 to generate a content request, which is provided to content management server 140. Content management server 140 provides app-specific content which relates to the predictions and is tailored to partner application 119. A display at user device 110 is then updated based on the app-specific content. FIG. 5 illustrates similar interactions, except that application coordination server 120 determines that its stored predictions are already current. Thus, the stored predictions are provided, and processing resources at genomics server 130 are conserved (e.g., because one or more polygenic models are not run).

Figure 6:
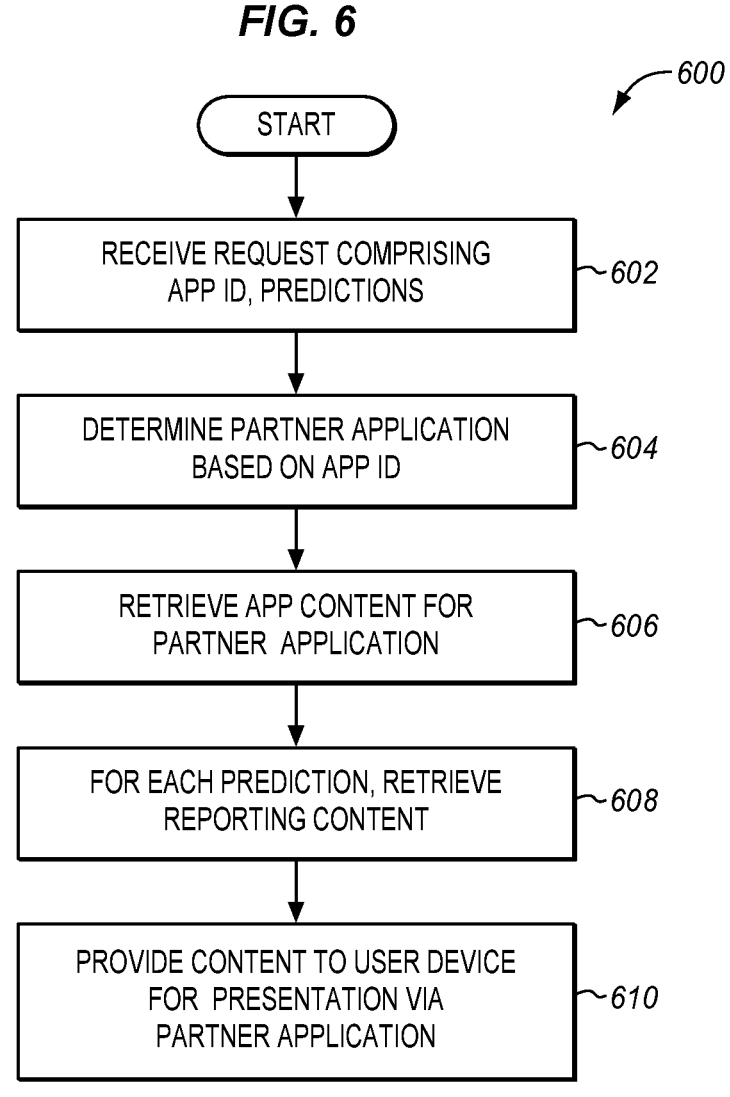
FIG. 6 is a flowchart depicting a method for retrieving content for a partner application in an illustrative embodiment.

FIG. 6 is a flowchart depicting a method 600 for retrieving content for a partner application in an illustrative embodiment. Method 600 may be performed, for example, during step 210 and/or 212 of method 200. According to method 600, in step 602 content management server 140 receives a request comprising an app IP and a list of predictions. The list of predictions may be provided as keys, which are names for traits, unaccompanied by accuracy estimates or confidence intervals. In step 604, controller 144 of content management server 140 determines which partner application content is being delivered for, based on the app ID.

In step 606, controller 144 retrieves app content for the partner application. For example, each app ID may be associated with its own library of content for retrieval from memory 146. Controller 144 retrieves app content related to the app ID. App content may include media such as text, logos, videos, or images. App content may also include style, formatting, and/or layout information indicating how to present content at a user device. For example, app content in the form of layout information may indicate how to arrange media for a partner application at a display. App content does not recite predictions. Hence, app content does not vary between individuals, but may vary between partner applications.

In step 608, for each prediction, controller 144 retrieves reporting content for the partner application. For example, memory 146 may store media relating to the characteristic of "hair color" in the form of unique textual and graphical media for each of "blonde hair," "brown hair," "red hair," "black hair," etc. By retrieving content specific to the predictions that were made, content that is tailored for the individual is provided. That is, reporting content is capable of varying (and is likely to vary) between individuals. Reporting content may include both media and layout information as described above for app content. In step 610, the app content and reporting content are provided to user device 110, for presentation via the partner application.

With descriptions provided for a variety of methods of operation of trait prediction system 100, FIGS. 7-12 illustrate various databases and tables which may be stored in memory at trait prediction system 100 in order to facilitate the operation of those methods.

FIG. 7 is a table 700 illustrating characteristics to predict on an application-by-application basis, in an illustrative embodiment. Each entry 710 in table 700 may include an app ID associated with a list of characteristics requested for prediction. For example, a fitness application may request predictions of cardiac health, muscle tone, and weight, while a family history application may request predictions for ancestry. Table 700 may be stored in memory 126 at application coordination server 120 in order to facilitate the selection of polygenic models.

FIG. 8 is a table 800 listing genetic records stored for individuals in an illustrative embodiment. Each entry 810 in table 800 indicates, for an individual recited in a target ID, the types of genetic records stored for that individual, and identifiers for genetic records stored for that individual. Thus, if multiple genetic records storing different pieces of genomic information are stored for an individual, they may be retrieved, combined, and used as input for a polygenic model.

FIG. 9 is a table 900 listing polygenic models for making predictions in an illustrative embodiment. Each entry 910 in table 900 recites a characteristic that the polygenic model makes a prediction for, a name for the model, and an intended target group for the model. The target group may be individuals within a particular demographic, individuals with a specific type of genetic records available, or may be based on other criteria.

FIG. 10 is a table 1000 illustrating predictions stored for individuals in an illustrative embodiment. Each entry 1010 in table 1000 includes a target ID indicating the individual that the prediction was made for, the characteristic that was predicted, and a prediction. The prediction includes allele data, a value indicating a likelihood of the prediction, a confidence interval, and a key labeling the prediction (e.g., "brown hair").

FIG. 11 illustrates content 1100 stored for a genomics application at a user device 110 in an illustrative embodiment. For example, content 1100 may be stored in memory 116 of user device 110. In this embodiment, the content is placed in a directory for the genomics application 118 in memory 116. The content includes an executable file for the genomics application, and resources for the genomics application. The resources include multiple libraries, icons for partner applications, and a Uniform Resource Identifier (URI) for each partner application. The icons are presented at the display 113 after the genomics application 118 has loaded. When a user selects an icon, the genomics application determines an app ID for the corresponding partner application based on a stored configuration file. After retrieving predictions based on the app ID, the genomics application may further use the URI for the partner application to retrieve content from a content management server.

FIG. 12 illustrates content 1200 stored for a partner application at a content management server in an illustrative embodiment. Content 1200 may be stored, for example, in memory 146 of content management server 140. According to FIG. 12, content for a partner application may include a URI for the partner application, Javascript Object Notation (JSON) content describing one or more pages within the partner application, and images, video, text, audio, and User Interface (UI) elements for the partner application. The text may include app text which is presented to all users, and reporting text which varies based on the particular predictions made for an individual.

Figure 14:
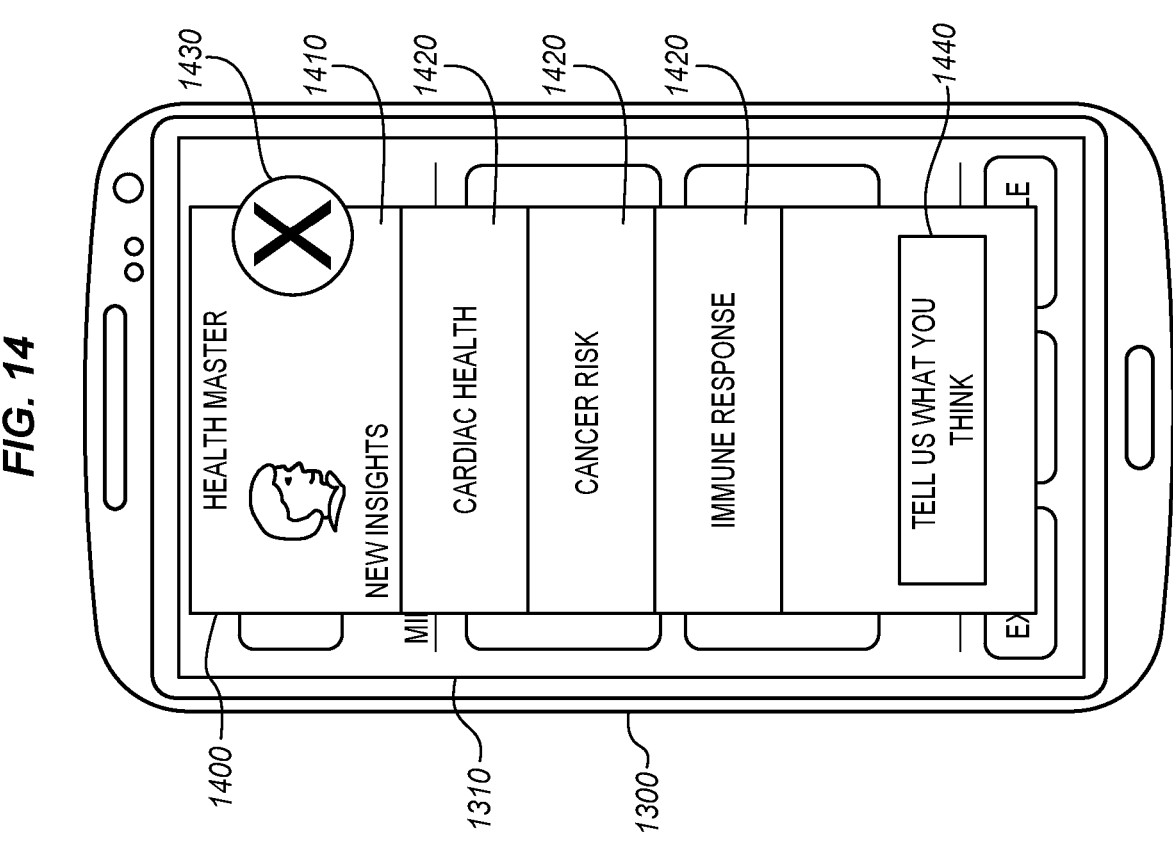
FIG. 14 illustrates a partner application displayed within a genomics application in an illustrative embodiment.
Figure 13:
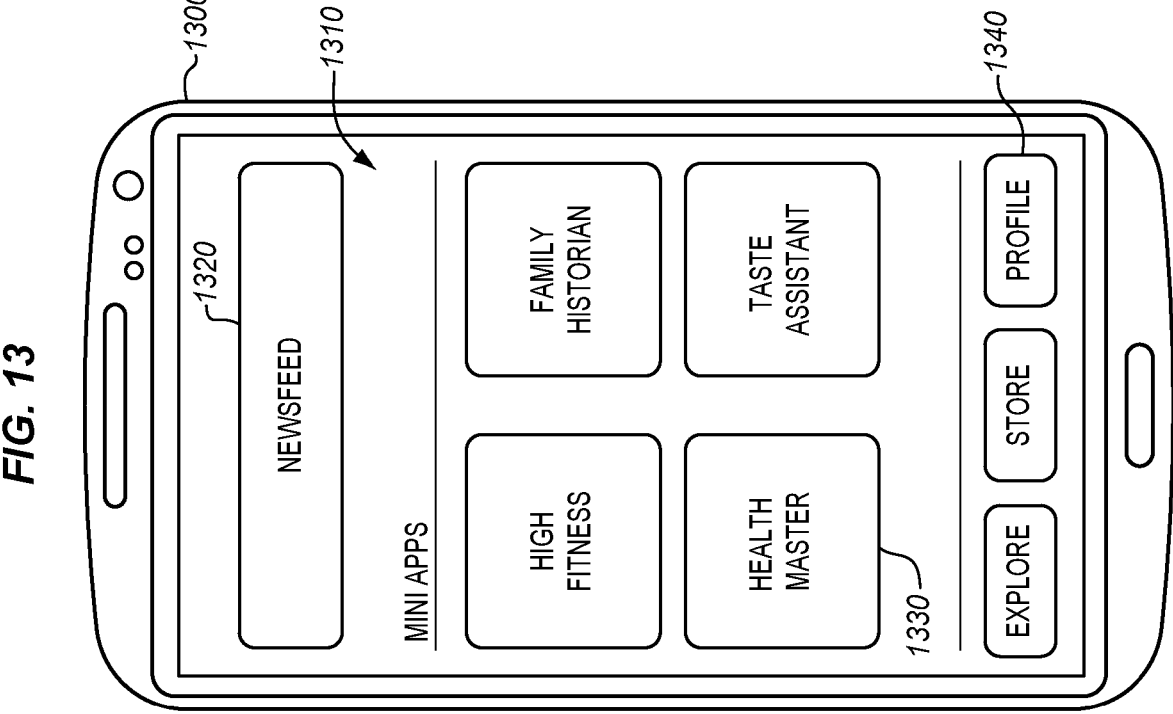
FIG. 13 illustrates a genomics application displayed at a user device in an illustrative embodiment.

FIGS. 13-14 illustrate how a partner application may be presented within a genomics application in an illustrative embodiment. FIG. 13 illustrates a genomics application 1310 displayed at a user device 1300 in an illustrative embodiment. According to FIG. 13, genomics application 1310 includes a newsfeed 1320 which displays current events or news related to genomic insights, and also includes multiple icons 1330 for launching partner applications. Genomics application 1310 further includes UI elements 1340 for performing various actions such as purchasing additional partner applications and editing a user profile.

FIG. 14 illustrates a partner application 1400 displayed within a genomics application in an illustrative embodiment. The partner application 1400 is displayed so that it appears to spring from (or otherwise be directly visually related to) genomics application 1310, which remains partially visible. Partner application 1400 includes its own news and insights section which may be tailored to the characteristics that are predicted by partner application 1400. Partner application 1400 also includes reporting content 1420, which indicates predictions on a characteristic by characteristic basis for an individual. A close button 1430 is placed prominently at the partner application, and when the close button is activated, user device 1300 returns to depicting genomics application 1310 as per FIG. 13. Feedback button 1440 is also included at partner application 1400. When feedback button 1440 is pressed, the present page for partner application 1400 is replaced by a new page asking for user feedback, but the close button 1430 remains prominently displayed. The new page keeps the same graphical relationship to genomics application 1310 as the originally presented page.

EXAMPLES

In the following examples, additional processes, systems, and methods are described in the context of a trait prediction system.

In this example, a genomics application is stored in the memory of a cell phone. The genomics application is launched by a processor within the phone that implements an Operating System (OS) based on instructions in memory. A user of the genomics application then enters login information which is authenticated via an application coordination server. Upon authorization, the application coordination server reports which partner applications are owned by the user. The genomics application displays icons for interacting with each of these partner applications. The number and type of icons presented via the genomics application therefore depends on the user that is presently logged in. The user selects an icon for a fitness partner application. In response to this action, the genomics application generates a request for predictions. The request is presented as a combination of application identifier and user identifier, and is encrypted. The request is provided to the application coordination server, which decrypts the request and determines which characteristics should be predicted for the fitness partner application. The characteristics for which predictions are desired are cardiac fitness and metabolic rate. The application coordination server also reviews metadata stored for the user which indicates that the user is female, that she has eastern European ancestry, and that she has genetic records for her exome (the protein-coding portions of the genome). The application coordination server determines that multiple polygenic models are available for predicting both characteristics using exome data. The application coordination server selects a polygenic model trained with a population of women (or optionally, women of eastern European ancestry) to generate predictions for cardiac fitness, and selects a polygenic model trained for the world at large to predict weight retention. The application coordination server contacts a genomics server, which runs the models to make predictions for the user, and predicts that the user has low cardiac health but also low likelihood of weight retention. The predictions are then forwarded to the cell phone.

At the cell phone, the processor operates instructions for the genomics application to generate a request transmitted to a content management server. The request indicates the specific predictions that were made for the user, and includes the application identifier. The content management server retrieves images and text for each prediction, and also retrieves JSON data indicating how to arrange the images and text on a display. This content is provided back to the cell phone. The processor at the cell phone updates the display with this content, while keeping the genomics application displayed behind the partner application. The user then views the predictions for their health, as interpreted via the partner application.

Figure 15:
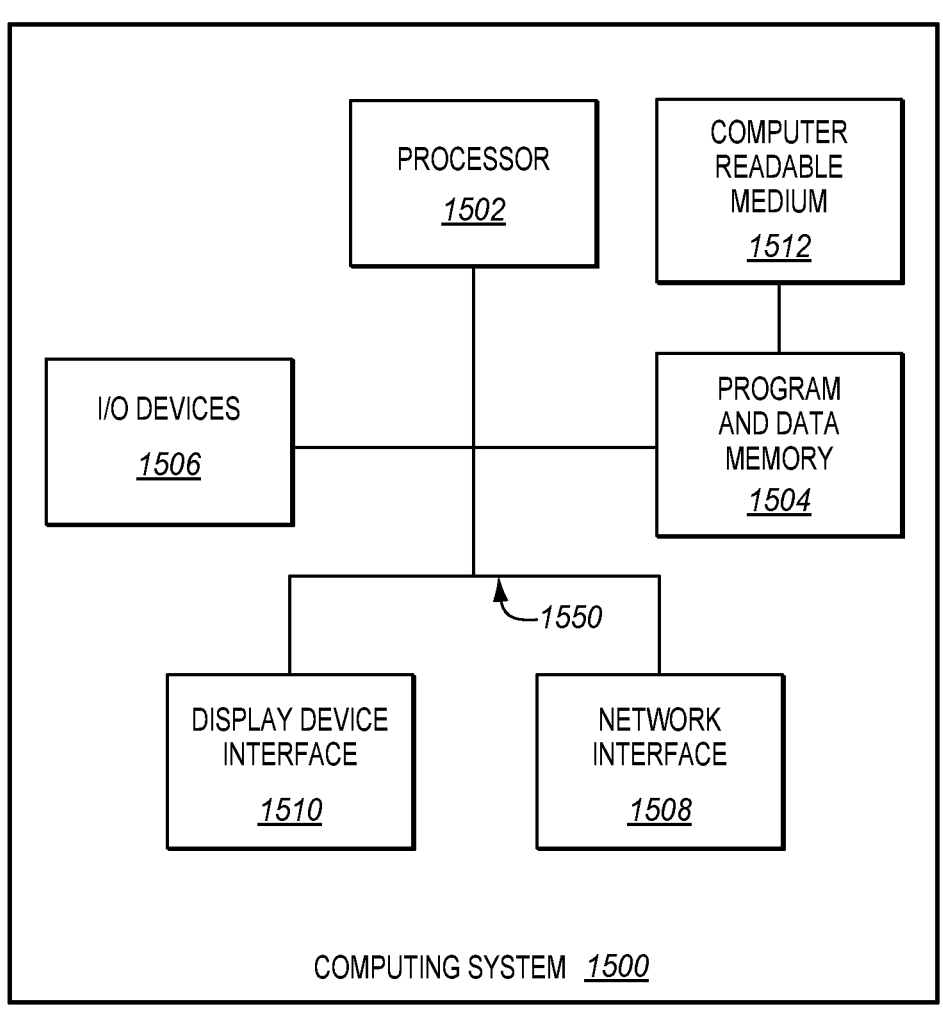
FIG. 15 depicts a computing system operable to execute programmed instructions embodied on a computer readable medium in an illustrative embodiment.

Embodiments disclosed herein can take the form of a hardware processor implementing programmed instructions, as hardware, as firmware operating on electronic circuitry, or various combinations thereof. In one particular embodiment, instructions stored on a computer readable medium are used to direct a computing system of user device 110, application coordination server 120, genomics server 130 and/or content management server 140 to perform the various operations disclosed herein. FIG. 15 illustrates an illustrative computing system 1500 operable to execute a computer readable medium embodying programmed instructions. Computing system 1500 is operable to perform the above operations by executing programmed instructions tangibly embodied on computer readable storage medium 1512. In this regard, embodiments of the invention can take the form of instructions (e.g., code) accessible via computer-readable medium 1512 for use by computing system 1500 or any other instruction execution system. For the purposes of this description, computer readable storage medium 1512 comprises any physical media that is capable of storing the program for use by computing system 1500. For example, computer-readable storage medium 1512 may be an electronic, magnetic, optical, electromagnetic, infrared, semiconductor device, or other non-transitory medium. Examples of computer-readable storage medium 1512 include a solid state memory, a magnetic tape, a removable computer diskette, a random access memory (RAM), a read-only memory (ROM), a rigid magnetic disk, and an optical disk. Current examples of optical disks include compact disk-read only memory (CD-ROM), compact disk-read/write (CD-R/W), and DVD.

Computing system 1500, which stores and/or executes the instructions, includes at least one processor 1502 coupled to program and data memory 1504 through a system bus 1550. Program and data memory 1504 include local memory employed during actual execution of the program code, bulk storage, and/or cache memories that provide temporary storage of at least some program code and/or data in order to reduce the number of times the code and/or data are retrieved from bulk storage (e.g., a spinning disk hard drive) during execution.

Input/output or I/O devices 1506 (including but not limited to keyboards, displays, pointing devices, etc.) may be coupled either directly or through intervening I/O controllers. Network adapter interfaces 1508 may also be integrated with the system to enable computing system 1500 to become coupled to other data computing systems or storage devices through intervening private or public networks. Network adapter interfaces 1508 may be implemented as modems, cable modems, Small Computer System Interface (SCSI)

devices, Fibre Channel devices, Ethernet cards, wireless adapters, etc. Display device interface 1510 may be integrated with the system to interface to one or more display devices, such as screens for presentation of data generated by processor 1502.

What is claimed is:

1. A system comprising:
a user device and an application coordination server communicatively coupled via a network; and
a genomics server configured to operate trained machine-learning polygenic models to make predictions about individuals based on one or more genetic records that report genetic variants for the individuals;
the user device comprising:
a memory configured to store a genomics application comprising an executable file, and partner applications;
a controller configured to launch the genomics application by executing the executable file, receive a selection by a user to present a partner application within the genomics application on a display of the user device, and generate a prediction request from the partner application that includes a target identifier for an individual and an application identifier that distinguishes the partner application from other partner applications; and
an interface configured to transmit the prediction request toward the application coordination server via the network; and
the application coordination server comprising:
an interface configured to receive the prediction request via the network; and
a controller configured to select characteristics to predict for the individual based on the application identifier, direct the genomics server to operate at least one of the trained machine-learning polygenic models to generate the predictions for the characteristics based on the genetic records stored at the genomics server for the individual, receive the predictions from the genomics server without receiving the genetic records, and generate a response to the prediction request that includes the predictions provided to the user device through the interface of the application coordination server;
wherein the controller of the user device is additionally configured to acquire media for presentation within the partner application based on the predictions, and operate the partner application to update the display at the user device with the media, thereby providing the predictions in a format specific to the partner application.

2. The system of claim 1 wherein:
the genomics server comprises:
an interface configured to receive the target identifier from the application coordination server; and
a controller configured to retrieve the genetic records stored for the individual based on the target identifier, and input the genetic records to the at least one of the trained machine-learning polygenic models to generate the predictions for the characteristics;
wherein the interface of the genomics server is configured to provide the predictions to the application coordination server.

3. The system of claim 1 wherein:
the media varies by partner application.

4. The system of claim 1 wherein:

the controller of the user device is further configured to acquire layout information indicating an arrangement of the media at the display.

5. The system of claim 1 wherein:

the trained machine-learning polygenic models use different combinations of predetermined genetic loci as input.

6. The system of claim 1 wherein:

the controller of the user device is further configured to acquire the media by:

reporting the application identifier and the predictions to a content management server; and receiving the media, from the content management server, that is associated with the partner application and the predictions.

7. The system of claim 6 wherein:

the memory of the user device is further configured to store a Uniform Resource Identifier (URI) for each of the partner applications; and the controller of the user device is further configured to use the URI corresponding with the partner application to acquire the media from the content management server.

8. The system of claim 1 wherein:

the controller of the user device is further configured to receive multiple commands to present a partner application within the genomics application, each command referring to a different partner application.

9. The system of claim 1 wherein:

the memory of the user device is further configured to store icons for the partner applications; and the controller of the user device is further configured to present the icons after the genomics application is launched, and determine the selection of the partner application by the user based on a selection of an icon corresponding with the partner application.

10. A method comprising:

storing, at a user device communicatively coupled to an application coordination server via a network, a genomics application comprising an executable file, and partner applications;

launching, at the user device, the genomics application by executing the executable file;

receiving a selection by a user at the user device to present a partner application within the genomics application on a display of the user device;

transmitting, from the user device to the application coordination server via the network, a prediction request from the partner application that includes a target identifier for an individual and an application identifier that distinguishes the partner application from other partner applications;

selecting, at the application coordination server, characteristics to predict for the individual based on the application identifier;

operating, at a genomics server in response to direction from the application coordination server, one or more trained machine-learning polygenic models to generate predictions for the characteristics based on genetic records that report genetic variants for individuals and that are stored at the genomics server for the individual;

providing, via the genomics server, the predictions to the application coordination server without providing the genetic records to the application coordination server;

providing the predictions from the application coordination server to the user device;

acquiring, at the user device, media for presentation within the partner application based on the predictions; and operating the partner application to update the display at the user device with the media, thereby providing the predictions in a format specific to the partner application.

11. The method of claim 10 wherein the operating at the genomics server comprises:

receiving the target identifier from the application coordination server;

retrieving the genetic records stored for the individual based on the target identifier; and inputting the genetic records to the one or more trained machine-learning polygenic models to generate the predictions for the characteristics.

12. The method of claim 10 wherein:

the media varies by partner application.

13. The method of claim 10 further comprising:

acquiring layout information indicating an arrangement of the media at the display.

14. The method of claim 10 wherein:

the trained machine-learning polygenic models use different combinations of predetermined genetic loci as input.

15. The method of claim 10 wherein:

acquiring the media comprises:

reporting the application identifier and the predictions to a content management server; and receiving the media, from the content management server, that is associated with the partner application and the predictions.

16. The method of claim 15 wherein:

the storing further comprises storing a Uniform Resource Identifier (URI) for each of the partner applications; and the acquiring the media comprises using the URI corresponding with the partner application to acquire the media from the content management server.

17. The method of claim 10 wherein:

selecting the characteristics to predict is performed by the application coordination server that is located remotely from the user device.

18. The method of claim 10 wherein:

the storing comprises storing icons for the partner applications; and the method further comprises:

presenting the icons after the genomics application is launched; and determining the selection of the partner application by the user based on a selection of an icon corresponding with the partner application.

19. A non-transitory computer readable medium embodying programmed instructions which, when executed by a processor, are operable for performing a method comprising:

storing, at a user device communicatively coupled to an application coordination server via a network, a genomics application comprising an executable file, and partner applications;

launching, at the user device, the genomics application by executing the executable file;

receiving a selection by a user at the user device to present a partner application within the genomics application on a display of the user device;

transmitting, from the user device to the application coordination server via the network, a prediction request from the partner application that includes a target identifier for an individual and an application identifier that distinguishes the partner application from other partner applications;

selecting, at the application coordination server, characteristics to predict for the individual based on the application identifier;

operating, at a genomics server in response to direction from the application coordination server, one or more trained machine-learning polygenic models to generate predictions for the characteristics based on genetic records that report genetic variants for individuals and that are stored at the genomics server for the individual;

providing, via the genomics server, the predictions to the application coordination server without providing the genetic records to the application coordination server;

providing the predictions from the application coordination server to the user device;

acquiring, at the user device, media for presentation within the partner application based on the predictions; and operating the partner application to update the display at the user device with the media, thereby providing the predictions in a format specific to the partner application.

20. The medium of claim 19 wherein the operating at the genomics server comprises:

receiving the target identifier from the application coordination server;

retrieving the genetic records stored for the individual based on the target identifier; and inputting the genetic records to the one or more trained machine-learning polygenic models to generate the predictions for the characteristics.

21. The medium of claim 19 wherein:

the media varies by partner application.

22. The medium of claim 19 wherein the method further comprises:

acquiring layout information indicating an arrangement of the media at the display.

23. The medium of claim 19 wherein:

the trained machine-learning polygenic models use different combinations of predetermined genetic loci as input.

24. The medium of claim 19 wherein:

acquiring the media comprises:

reporting the application identifier and the predictions to a content management server; and receiving the media, from the content management server, that is associated with the partner application and the predictions.

25. The medium of claim 24 wherein:

the storing further comprises storing a Uniform Resource Identifier (URI) for each of the partner applications; and the acquiring the media comprises using the URI corresponding with the partner application to acquire the media from the content management server.

26. The medium of claim 19 wherein:

the storing comprises storing icons for the partner applications; and the method further comprises:

presenting the icons after the genomics application is launched; and determining the selection of the partner application by the user based on a selection of an icon corresponding with the partner application.

* * * * *